United States Patent [19]

Mayer

[11] Patent Number: 4,485,918
[45] Date of Patent: Dec. 4, 1984

[54] NEEDLE DISPOSAL APPARATUS

[76] Inventor: Theodore Mayer, 256 Inwood Dr., Rochester, N.Y. 14625

[21] Appl. No.: 598,066

[22] Filed: Apr. 9, 1984

[51] Int. Cl.$^3$ ............... B65D 25/00; B65F 1/02; B65F 7/00; A61M 5/32
[52] U.S. Cl. ............... 206/366; 206/63.5; 206/370; 206/380; 206/216
[58] Field of Search ............... 206/370, 366, 365, 380, 206/216, 63.5

[56] References Cited

U.S. PATENT DOCUMENTS

| | | | |
|---|---|---|---|
| 3,893,608 | 7/1975 | Koenig | 206/366 |
| 4,296,786 | 10/1981 | Brignola | 206/365 |
| 4,332,323 | 6/1982 | Reenstierna | 206/365 |
| 4,351,434 | 9/1982 | Elisha | 206/63.5 |
| 4,375,849 | 3/1983 | Hanifl | 206/63.5 |
| 4,452,358 | 6/1984 | Simpson | 206/366 |

Primary Examiner—William T. Dixson, Jr.
Attorney, Agent, or Firm—Warren W. Kurz

[57] ABSTRACT

Apparatus for facilitating the safe disposal of used hypodermic needles. According to a preferred embodiment, a funnel-like member, adapted to be hand-held, functions to support a needle sheath during a needle-sheathing operation. The converging walls of such member shield the hand of the user from accidental "needle sticks". Also disclosed are needle containers which incorporate means for facilitating the sheathing of used needles prior to entering the container.

9 Claims, 8 Drawing Figures

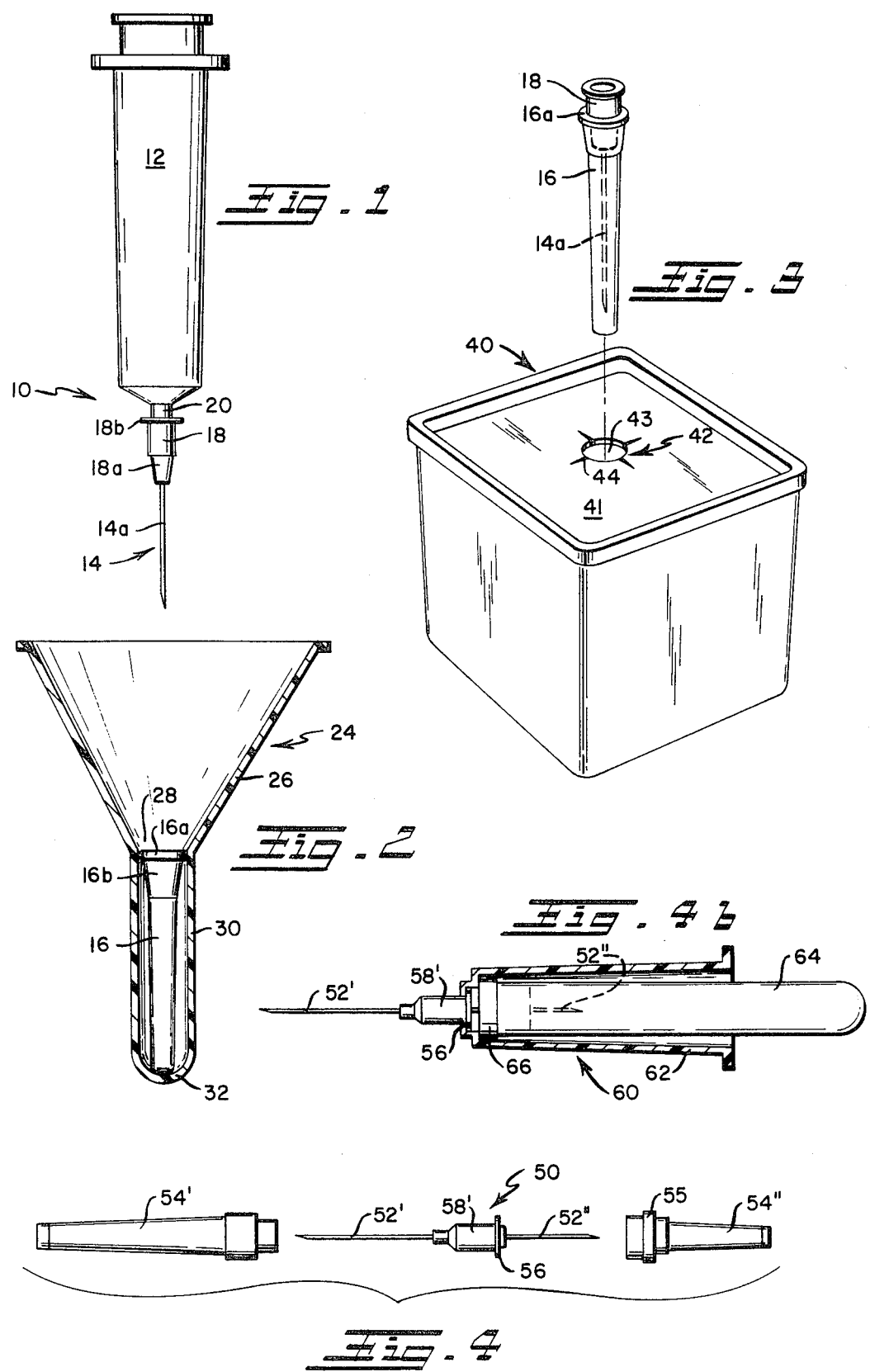

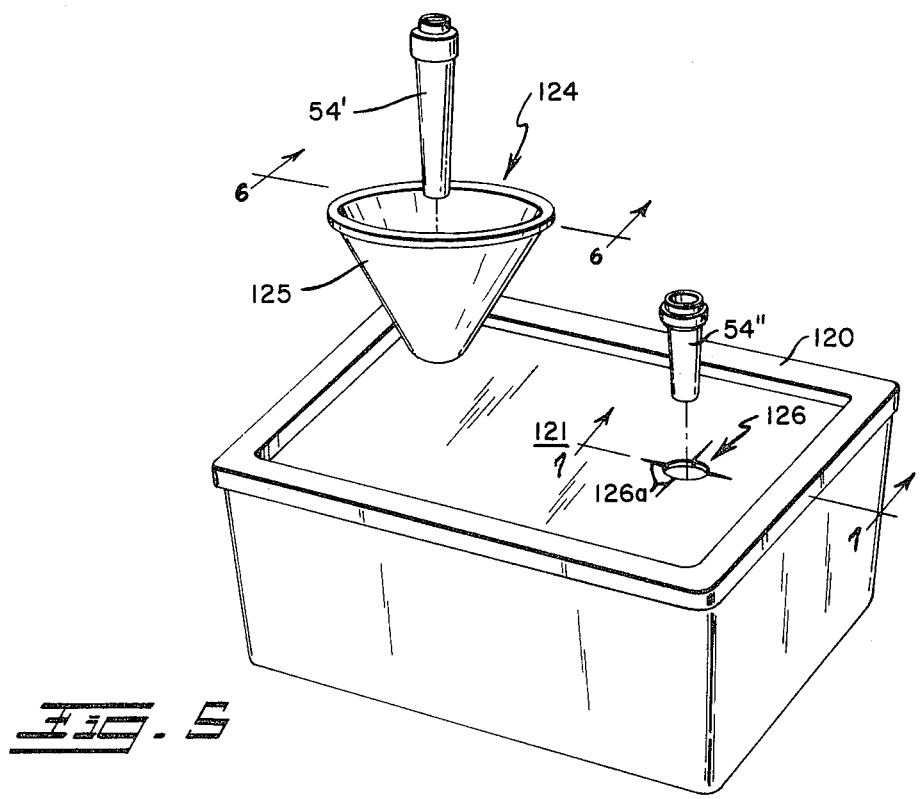
Fig. 5
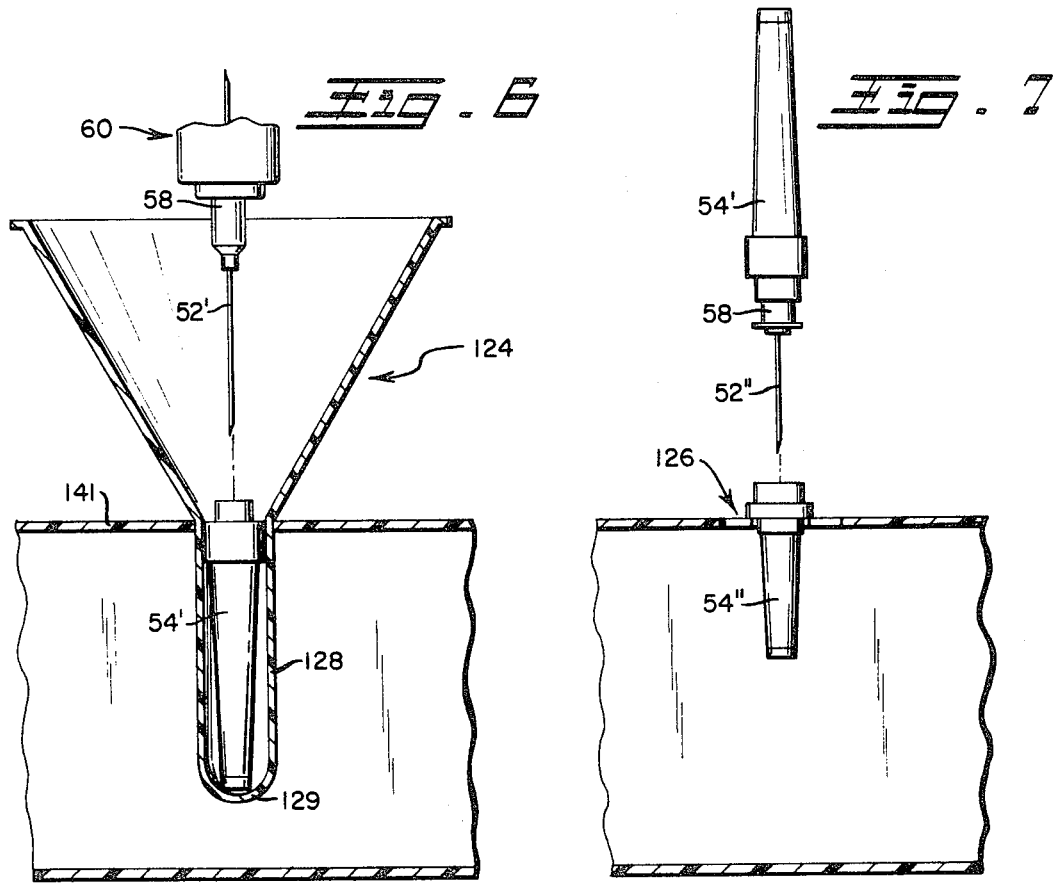
Fig. 6
Fig. 7

NEEDLE DISPOSAL APPARATUS

BACKGROUND OF THE INVENTION

This invention relates to improvements in apparatus for safely disposing of used hypodermic needles. More particularly, it relates to apparatus by which the resheathing of a used hypodermic needle is facilitated prior to collection, for example, in a sealed container.

After use, the tip of a hypodermic needle may bear a wide variety of diseases (e.g. hepatitis, Acquired Immune Deficiency Syndrome (AIDS), etc.) which can be communicated to one who is accidentally pricked or stuck by it. So prevalent are such accidental "needle sticks", as they are commonly known in hospital parlance, that some estimates suggest that millions of dollars per year are spent in running blood tests following needle sticks to verify that a disease may have (or have not) been communicated, and to prophylactically treat potential disease if such tests are positive. This cost, of course, is reflected in increased medical bills to all of us.

Frequently, needle sticks occur while a nurse or medical technician attempts to return the used needle to its protective sheath prior to disposal. Such resheathing is considered by most to be an essential first step in the safe disposal of used needles. Unfortunately, resheathing a used needle has proven to be no simple task, especially when it must be performed under the pressures and time constraints common in busy hsopitals and medical practices. To obviate the need for resheathing, considerable effort has been expended in devising devices which dispose of needles without sheaths. Some such devices comprise containers which, upon receiving a needle through an aperture, strip the needle from its syringe faucet and retain it. See, for example, U.S. Pat. No. 4,351,434 issued to Elisha in 1982, and U.S. Pat. No. 3,876,067 issued to Schwarz in 1975. While such containers facilitate needle disposal for the immediate user, they can be costly to produce and consume considerable space. Furthermore, since the needles collected in such containers have no sheaths, they can present a substantial hazzard to the immediate user, especially when the container is nearly full and one attempts to jam more needles into it, as well as to those further down the needle disposal chain, e.g. refuse collectors, who ultimately dispose of the needles in an incinerator.

The most common type of blood-drawing needles have two juxtaposed needle elements, one being used to draw blood and the other being used to penetrate the septum of an evacuated tube (e.g., a "Vacutainer" tube, trademark of Becton-Dickinson) for the purpose of collecting the drawn blood. This type of hypodermic needle presents an even more difficult problem of safe disposal, especially so if both needle elements are to be resheathed prior to collection for disposal. To date, it is common to dispose of such needles, with or without sheaths, by merely dropping them in a sealed container. As noted above, unsheathed needles can present a health hazard to those who ultimately destroy the needles, and the task of resheathing both needle elements prior to disposal presents a substantial health hazard to those effecting the resheathing operation.

SUMMARY OF THE INVENTION

In view of the foregoing, it is an object of the invention to provide an apparatus which facilitates the safe resheathing of used hypodermic needles prior to disposal.

Another object of this invention is to provide a container for used hypodermic needles which facilitates the resheathing of needles as they enter such container.

A further object of this invention is to provide a container for used hypodermic needles of the two-element type (e.g. for blood drawing and collecting) which container includes means for facilitating resheathing of both ends of the needle prior to receiving and containing the resheathed needles.

One of the above objects of the invention is achieved by the provision of a funnel-shaped member which is adapted to receive and support the sheath of a hypodermic needle. Such funnel-shaped member comprises (a) an endless wall portion which converges toward an apex, such wall portion being truncated before reaching the apex to form a relatively narrow aperture, and (b) a substantially tubular portion having an inside diameter slightly greater than a needle sheath. The tubular portion has an open end which communicates with the aperture of the converging wall portion, and a constricted end which prevents a sheath entering the tubular portion through the aperture from passing therethrough. In use, the funnel-shaped member may be hand-held and, during resheathing of a needle with a sheath positioned within the tubular portion, the wall portion shields the hand from accidental needle sticks.

Another object of the invention is achieved by the provision of a container having a wall portion in which there is provided means for facilitating the resheathing of a hypodermic needle. Such facilitating means comprises means for releasably retaining a needle sheath, such retaining means being operable to retain a sheath while a needle is moved in a direction relative thereto to effect sheathing of the needle with the retained sheath, and to release the sheathed needle into the container upon continued movement of the needle in the sheathing direction. Optionally, the wall portion of the container also comprises means for supporting a funnel-shaped member of the type described. The combination of the funnel-shaped member and the releasable retaining means is particularly useful in resheathing both needle elements of a conventional blood drawing/collecting needle prior to collection in the container.

The invention and its various advantages will become evident to those skilled in the art from the ensuing detailed description of preferred embodiments, reference being made to the accompanying drawings.

BRIEF DESCRIPTION OF THE DRAWINGS

FIG. 1 is a side elevation of a hypodermic needle assembly;

FIG. 2 is a cross-sectional view of a preferred embodiment of the invention;

FIG. 3 is a prespective view of a preferred container for receiving sheathed needles;

FIGS. 4a and 4b illustrate conventional two-element blood-drawing needles, prior to and during use, respectively;

FIG. 5 is a perspective view of another preferred embodiment of the invention; and FIGS. 6 and 7 are cross-sectional views of the apparatus shown in FIG. 5, taken along the section lines 6—6 and 7—7, respectively.

DETAILED DESCRIPTION OF PREFERRED EMBODIMENTS

Referring now to the drawings, FIG. 1 shows a conventional hypodermic needle assembly 10 comprising a syringe 12 and a needle element 14. Needle element 14 comprises a hollow needle shank 14a coupled to a hub 18 which, in use, is press-fit over a spigot 20 of the syringe 12. Prior to use, the needle shank is provided with a protective sheath 16 (shown in FIG. 2). Sheath 16 has an enlarged open end 16a which is sized to receive a tapered portion 18a of the needle element's hub 18. When the sheath is applied, the needle shank 14a and the hub's tapered portion 18a are housed in the sheath, as shown in FIG. 3. In preparation for use, the sheath is removed and, following use and prior to disposal of the needle element, it is desirable, as noted above, to reapply the sheath to the needle shank.

According to one aspect of the invention, there is provided a funnel-like member 24, shown in FIG. 2, for facilitating the resheathing operation. Such member is preferably made of a hardened plastic material (e.g., polytetrafluoroethylene) so as to be non-penetrable by a needle tip. Member 24 has an endless wall portion 26 which converges toward an apex A. Before reaching such apex, however, wall portion 26 (which may have a circular or polygonal (e.g., triangular, rectangular or hexagonal) cross-section) is truncated to provide an aperture 28. A tubular member 30, having a constricted or closed end 32 and an open end 34, is coupled to member 24 so that its open end communicates with aperture 28. The inside diameter of tubular member 30 is slightly greater than the outside diameter of the needle sheath, so that a sheath can loosely fit inside the tubular member. The length of the tubular member is approximately equal to the length of the sheath, so that the flanged open end of the sheath is approximately co-planar with the plane of aperture 28 when a sheath is positioned within the tubular member, as shown in FIG. 2.

In use, funnel-like member 24 may be hand-held with the user's hand gripping member 30. A sheath, once removed from the needle element, is dropped into the funnel-like member 24 so that the sheath's closed end abuts the closed end of the tubular member and is supported thereby. During the resheathing operation, the user's hand is shielded from the needle tip by wall portion 24 as the needle tip is moved toward the sheath's open end. As the needle enters the sheath, the closed end of tubular member 30 prevents axial movement of the sheath away from the needle. After the tapered portion of the needle hub 18 is firmly seated in the enlarged open end of the sheath, the sheathed needle can be withdrawn from the funnel-like member. Funnel-shaped member 24 is particularly useful, for example, at a patient's bedside, as it may be placed conviently nearby on a night stand until needed. By having flat sides (i.e., a polygonal cross-section), it is prevented from rolling away.

Referring to FIG. 3, there is shown a container 40 having a wall portion 41 (preferably its top) in which means 42 are provided for facilitating the sheathing operation discussed above. Wall portion 41, and preferably the entire container is made of a flexible material, such as a thin guage (e.g., 1 mm. thick) plastic, which is not readily penetrated by a needle tip. Preferred plastics are polypropylene and polytetrafluoroethylene. Means 42 is in the form of an aperture 43 which is sized to receive and releasably support sheath 16. When used with the type of sheath shown in FIG. 1, the diameter of aperture 43 is approximately equal to the diameter of hub 16b, so that a received sheath is supported by its flange 16a.

In use, a sheath 16 is removed from an assembled hypodermic needle assembly 10 and inserted in aperture 43. The syringe 12 component having a needle element 18 fitted thereon is moved toward the flanged open end of the sheath. The needle shank enters and moves within the sheath until hub 18 abuts the flanged end of the sheath. At this point the tapered hub portion 18a becomes press-fit with the interior of the sheath's hub 16b. Continued movement of the syringe toward the sheath causes the aperture to flex and thereby enlarge. To facilitate the enlargement of aperture 43, radially-extending slots 44 are formed in wall portion 41. Aperture 43 enlarges until the sheath's flange passes therethrough, whereupon the aperture snaps back to its original (i.e., unflexed) size which allows the flanged hub 18 of the needle element to pass. After hub 18 enters the container, the syringe is moved laterally to position flange 18b behind the wall portion 41. Movement of the syringe away from the container causes the sheathed needle to be stripped from the spigot 20 and deposited in the container. It will be appreciated that during the sheathing operation there is no risk of a needle stick to the user, and that the needle is sheathed before it enters the container. Also, the container can be used to receive pre-sheathed needles, such as needles which have been sheathed by the apparatus shown in FIG. 2.

Referring now to FIG. 4a, a conventional blood drawing needle 50 is shown to comprise two juxtaposed needle elements 52' and 52", each having its own sheath 54' and 54", respectively. Both needle elements have hollow shanks which communicate, blood being drawn into element 52' and exiting through element 52". Needle hub 58 is provided with a bayonet connector 56 which serves to connect needle 50 to a syringe 60, as shown in FIG. 4b. Syringe 60 comprises a container 62 which, during use, supports an evacuated tube 64 having a rubber septum 66 sealing its open end. When needle element 52' is inserted in a vein, tube 64 is moved toward element 52" so that element 52" penentrates the septum. By virtue of the vacuum in tube 64, blood is drawn through the needle elements and deposited in the tube. As indicated above, it is highly desirable to resheath both needle elements after use and prior to disposal.

In FIGS. 5–7, there is shown apparatus for facilitating the safe disposal of two element needles of the type shown in FIGS. 4a and 4b. Such apparatus comprises a container 120 having a construction similar to that described above. Container 120 has a wall portion 121 in which there is provided means for facilitating the resheathing of both needle elements prior to receipt by the container. Such means comprises a funnel-like member 124 of the type described above, and an expandable aperture 126. The tubular portion 128 of member 124 is sized to receive the sheath 54' for the blood drawing needle element 52' (as shown in FIG. 6) and aperture 126 is sized to releasably support the sheath for the blood collecting needle element 52" (as shown in FIG. 7).

In the following description of the manner in which the apparatus of FIGS. 5–7 is used, it is assumed that the needle 50 is initially sheathed at both ends, this being the manner in which such needles are conventionally supplied. The user first removes sheath 54" and inserts it into aperture 126 so that the sheath's flange 55 is supported by the wall portion 121 surrounding the aperture. Holding the needle 50 by its sheath 54', the user then inserts needle element 52" into container 62, making the bayonet connection. Thereafter, sheath 54' is removed from needle element 52', and this sheath is dropped into the tubular portion 30 of member 124, as shown in FIG. 6. After the blood drawing/collection operation, needle element 52' is resheathed (while still attached to the syringe 60) by inserting it into its sheath 54' while this sheath is supported by member 128. The closed end 129 of member 128 enables a press-fit coupling to be made between the sheath and a portion of hub 58. Upon sheathing element 52', needle 50 is decoupled from container 62 by holding the sheath 54' and turning it relative to the container. The exposed needle element 52" is then inserted into sheath 54", as shown in FIG. 7. Aperture 126 retains sheath 54" until a press-fit is established with the needle hub 58, and thereafter releases the fully sheathed needle assembly into the interior of container 120. Slots 126a are provided to reduce the force required to pass the sheathed needle asembly into the container.

The invention has been described with particular reference to preferred embodiments. It will be appreciated, of course, that variations can be made without departing from the spirit and scope of the invention. For example, member 124 shown in FIG. 5 need not have the converging wall portion 125. While this costruction facilitates placement of a sheath in the lower tubular portion and even acts as a guide in the subsequent resheathing operation, it does not lower the risk of needle sticks since, in the FIG. 5 embodiment, it is not intended to be hand-held. Similarly, other modifications will occur to those skilled in the art.

I claim:

1. Apparatus for use in applying a tube-like sheath to a hypodermic needle, said apparatus comprising a funnel-like member adapted to receive and support a sheath, said member having (a) an endless wall portion which converges toward an apex, said wall portion being truncated before reaching said apex to form a relatively narrow aperture, and (b) a substantially tubular portion having an inside diameter slightly greater than the sheath diameter, said tubular portion having an open end which communicates with said aperture and a constricted end which prevents a sheath entering said tubular portion through said aperture from passing therethrough.

2. The apparatus according to claim 1 wherein the distance between said open and constricted ends is substantially equal to the length of the sheath to be applied.

3. A container for receiving and containing sheathed hypodermic needles, said container comprising a wall portion and means associated therewith for releasably retaining a needle sheath, said retaining means being operable to retain a sheath while a needle is moved in a direction relative thereto to effect sheathing of the needle with such sheath, and to release the sheathed needle into said container upon continued movement of the needle in said direction.

4. The container as defined by claim 3 wherein said releasably retaining means comprises means defining an aperture in said wall portion, said aperture being sized and shaped to snuggly surround a needle sheath.

5. A container for receiving and containing sheathed hypodermic needles, said container comprising a wall portion and means associated with said wall portion for facilitating the resheathing of both needle elements of a sheathless hypodermic needle of the type having juxtaposed first and second needle elements, each needle element having its own protective sheath which is to be applied before entering said container.

6. The container as defined in claim 5 wherein said facilitating means comprises (a) means coupled with a wall portion of the container for releasably supporting a first sheath for the first needle element of said hypodermic needle, said supporting means comprising means for preventing substantial axial movement of said first sheath in the direction in which a first needle element enters said first sheath to effect resheathing thereof, said supporting means allowing axial movement in the opposite direction to allow removal of the sheath from said support means after the resheating of said first needle element has been effected.

7. The container as defined by claim 6 wherein said facilitating means further comprises means defining an aperture in said wall portion for releasably retaining a second sheath for the second needle element of said hypodermic needle, said aperture being of a size and shape to yieldably resist substantial axial movement of said second sheath in the direction in which a second needle element enters said second sheath to effect resheathing thereof, and to pass the resheathed first and second needle elements to the interior of the container.

8. The container as defined by claim 3 wherein said wall portion is flexible to allow enlargement of said aperture to permit entry of the sheathed hypodermic needle into said container.

9. A container for receiving and containing sheathed hypodermic needles, said container comprising means for facilitating the resheathing of hypodermic needles of the type having juxtaposed first and second needle elements, each needle element having its own protective sheath which is to be applied before a hypodermic needle enters said container, said facilitating means comprising: (a) first means coupled with a wall portion of the container for releasably supporting a first sheath for the first needle element of the hypodermic needle, said first means comprising means for preventing substantial axial movement of said sheath while a hypodermic needle is moved relative thereto to effect sheathing of its first needle element, said support means allowing movement of said first sheath in a direction opposite such sheathing movement to allow removal of the first sheath from the support means, and (b) means defining an aperture in said wall portion for releasably retaining the sheath for the second needle element, said aperture being dimensioned and shaped to retain said sheath while said second needle element is moved relative thereto to effect sheathing thereof and to pass the resheathed first and second needle elements to the interior of the container.

* * * * *